United States Patent [19]

Bandurco et al.

[11] Patent Number: 4,711,883

[45] Date of Patent: Dec. 8, 1987

[54] SUBSTITUTED 3-(4-PHENYL-1-PIPERAZINYL)ALKYL-QUINAZOLIN-2,4-(1H,3H) DIONES, METHODS OF PREPARATION, COMPOSITIONS AND METHOD OF USE

[75] Inventors: Victor T. Bandurco, Bridgewater; Charles F. Schwender, Califon; Robert Falotico, Belle Mead, all of N.J.; Alfonso J. Tobia, Doylestown, Pa.

[73] Assignee: Ortho Pharmaceutical Corporation, Raritan, N.J.

[21] Appl. No.: 782,241

[22] Filed: Sep. 30, 1985

[51] Int. Cl.$^4$ .................. A61K 31/505; C07D 403/06
[52] U.S. Cl. ..................................... 514/253; 544/285
[58] Field of Search .................. 544/285; 514/253

[56] References Cited

PUBLICATIONS

Havera, I, "Chemical Abstracts", vol. 91(25), 1979, Col. 204216p.
Havera II, "Chemical Abstracts", vol. 82(25), 1975, col. 171029p.
Parcell, "Chemical Abstracts", vol. 80(25), 1974, col. 146190k.

*Primary Examiner*—Glennon H. Hollrah
*Assistant Examiner*—James H. Turnipseed
*Attorney, Agent, or Firm*—Benjamin F. Lambert

[57] ABSTRACT

Novel substituted-3-(4-phenyl-1-piperazinyl)alkyl quinazolin-2,4-(1H,3H)diones are described. These compounds are useful as antihypertensive agents.

12 Claims, No Drawings

SUBSTITUTED 3-(4-PHENYL-1-PIPERAZINYL)ALKYLQUINAZOLIN-2,4-(1H,3H) DIONES, METHODS OF PREPARATION, COMPOSITIONS AND METHOD OF USE

BACKGROUND OF THE INVENTION

1. Field of the Invention

This invention relates to certain substituted -3-(4-phenyl-1-piperazinyl)alkylquinazolin-2,4-(1H, 3H) diones. These compounds are antihypertensive and cardiovascular agents and are therefore useful in male and female mammals. This invention also relates to a process for preparing these compounds, to compositions thereof and to methods of use.

2. Related Disclosures

Several quinazolin-2,4-(1H,3H) diones having vasodilator, alpha$_1$-blocking or antihypertensive activity have been reported in the literature. Examples thereof are U.S. Pat. No. 3,879,393; European Pat. No. 89065-A; U.S. Pat. No. 3,919,425 and J. Med. Chem. 8, 807 (1965); German Pat. No. 2,258,403 (June 7, 1973); and U.S. Pat. No. 4,405,623. None of the above reported quinazolinediones contain all of the specific substituents presently claimed.

SUMMARY OF THE INVENTION

The substituted quinazolin-2,4-(1H,3H) diones which are the subject of this invention have the following general formula:

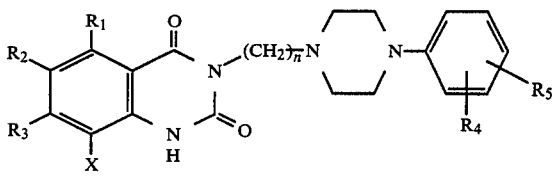

I wherein
X is hydrogen, amino, nitro, acetamido or halo;
$R_1$ and $R_3$ are the same or different and are hydrogen. hydroxy or alkoxy;
$R_2$ is hydroxy or alkoxy; or when $R_1$ and $R_2$ or $R_2$ and $R_3$ are taken together they are lower alkylenedioxy;
n is an integer from 2 to 6;
$R_4$ and $R_5$ are the same or different and are hydrogen, hydroxy, alkyl, alkoxy, halo, or trifluoromethyl; or when $R_4$ and $R_5$ are taken together they are lower alkylenedioxy; or the pharmaceutically acceptable acid addition salts thereof.

Also included in this invention is a process for preparing the compounds of formula I which comprises reacting a compound of the formula

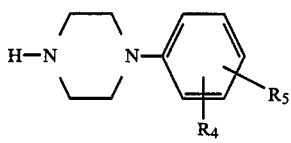

V with a compound of the formula

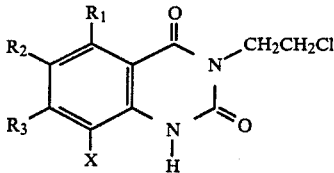

IV wherein $R_1$, $R_2$, $R_3$, $R_4$, $R_5$ and X are as defined above in connection with the product.

Also part of the present invention are certain intermediates and the processes for the preparation thereof.

Preferred compounds of the present invention are:
3-{2-[4-(2-methoxyphenyl)-1-piperazinyl]ethyl}-5,6-dimethoxy-quinazolin-2,4(1H,3H)-dione;
8-chloro-3-{2-[4-(2-methoxyphenyl)-1-piperazinyl]ethyl}-5,6-dimethoxyquinazolin-2,4-(1H,3H)-dione;
6,7-dimethoxy-3-{2-[4-(2-methoxyphenyl)-1-piperazinyl]ethyl}-quinazolin-2,4-(1H,3H)dione;
5,6-dihydroxy-3-{2-[4-(2-methoxyphenyl)-1-piperazinyl]ethyl}-quinazolin-2,4-(1H,3H)dione.

The compounds of this invention possess oral hypotensive activity in spontaneously hypertensive rats and peripheral vasodilator activity in dogs through, at least in part, an $\alpha_1$-adrenergic antagonist mechanism. When compared to the prior art, such as a representative compound of the above-mentioned European Pat. No. 89065-A, (set forth in Table 1 herein), the present compounds show less inhibition of the tilt reflex response suggesting that the compounds will be better tolerated in humans due to a lesser potential for orthostatic hypotension. In addition, they show an unexpected superior bioavailability profile over prior art when the oral/i.v. ratios are compared.

The compounds, compositions and methods for making the various aspects of the present invention noted above will become more readily apparent from the following description.

DESCRIPTION AND PREFERRED EMBODIMENTS

Various terms used herein should be understood to signify the following.

The term "lower alkyl" refers to a straight or branched chain substituent consisting solely of carbon and hydrogen with no unsaturation and containing from 1 to 6 carbon atoms. The term "lower alkoxy" refers to a lower alkyl chain as described above having no more than 4 carbons. The term "halo" means fluoro chloro, bromo and iodo.

The phrase "pharmaceutically acceptable salts" denotes salts of the free base which possess the desired pharmacological activity of the free base and which are neither biologically nor otherwise undersirable. These salts may be derived from inorganic or organic acids. Examples of inorganic acids are hydrochloric acid, nitric acid, hydrobromic acid, sulfuric acid or phosphoric acid. Examples of organic acids are acetic acid, propionic acid, glycolic acid, lactic acid, pyruvic acid, oxalic acid. malonic acid, succinic acid, malic acid, maleic acid, fumaric acid, tartaric acid, citric acid, benzoic acid, cinnamic acid, mandelic acid, methane sulfonic acid, ethane sulfonic acid, p-toluene sulfonic acid, salicylic acid and the like.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g. intravenous, oral or topical. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case or oral solid preparations such as, for example. powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.05 to about 100 mg/kg and preferably from about 0.1 to about 20 mg/kg of the active ingredient.

The novel quinazoline diones of the present invention may be synthesized according to the following reaction scheme wherein $R_1$, $R_2$, $R_3$, $R_4$, $R_5$, $R_6$, and X are as defined above and Q is a leaving group which is most preferably ethoxy.

appropriately substituted ethyl 2-amino-benzoate with ethyl chloroformate and a suitable base such as triethylamine in a suitable solvent such as tetrahydrofuran, dioxane or no additional solvent.

The resultant appropriately substituted ethyl N-[2-carbethoxy phenyl]carbamate is then reacted with ethanolamine at approximately 160°-170° C. for between 30 minutes and 60 minutes.

The resultant product of formula III is then treated with a suitable chlorinating agent such as thionyl chloride. The chlorination reaction takes place in a suitable solvent such as chloroform or methylene chloride, preferably under reflux for between 1 and 5 hours under nitrogen. The resultant compound IV is a novel compound, as is also compound III.

Compound IV is then reacted with compound V in order to produce compound I. The reaction preferably takes place in the presence of sodium iodide and potassium carbonate in a solvent such as dimethylformamide (DMF) or 4-methyl-2-pentanone at a temperature of between about 80° and 85° C. under nitrogen for about 1-36 hours.

In the instance wherein substituents $R_1$, $R_2$, and $R_3$ are loweralkoxy, such substituents may be hydrolyzed to the corresponding hydroxyl groups by reacting the appropriately substituted compound of formula I under reflux for about 24 hours in an acidic medium, preferably a mixture of hydrobromic acid and acetic acid. However, other acidic media such as HI, $BBr_3$, pyridine hydrochloride or 47% HBr, may also be used. When this procedure is carried out any lower alkoxy group on the phenyl ring attached to the piperazine ring, remains unaffected.

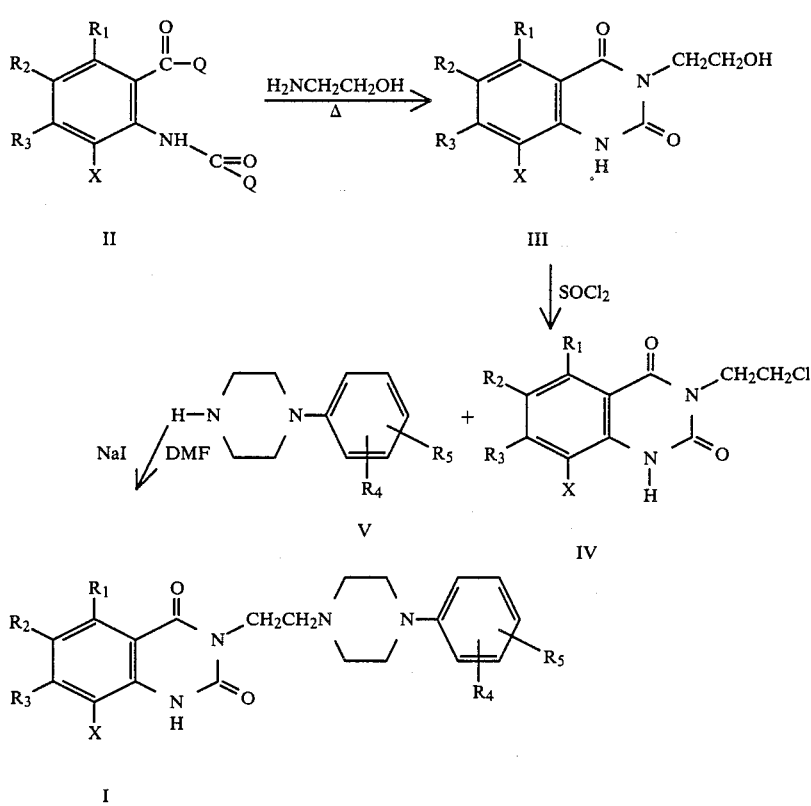

Compound II, in the reaction scheme above, may be initially prepared by reacting a cooled solution of an The following specific preparations and examples are illustrative of the present invention and should not be considered as limitative thereof in any manner.

PREPARATION 1

Ethyl N-[2-carbethoxy-4,5-dimethoxyphenyl]carbamate

The following preparation illustrates the conversion of 2-amino-4,5-dimethoxybenzoate to compound II, in the instance wherein Q is ethoxy.

Ethyl chloroformate (10.4 g, 0.096 mole) was added to a cooled solution containing 6.5 g (0.028 mole) of ethyl 2-amino-4,5-dimethoxybenzoate, 6.6 g (0.065 mole) of triethylamine and 90 ml of tetrahydrofuran. The resultant reaction mixture was allowed to warm to room temperature and stirred for 2.5 hours. The reaction mixture was filtered and the filtrate was evaporated to give a yellow gum which was crystallized from hexane giving 4.0 g (46.6%) of desired product, mp 59°–61° C.

EXAMPLE 1

3-(2-Hydroxyethyl)-5,6-dimethoxyquinazolin-2,4-(1H,3H)dione

This example illustrates the preparation of compounds of formula III.

A mixture of ethyl N-[2-carbethoxy-3,4-dimethoxyphenyl]carbamate (2.2 g, 0.006 mole) and ethanolamine (0.8 g, 0.013 mole) was heated at 160°–170° C. in an oil bath for 0.5 hours. The semisolid which formed was triturated with 2-propanol and the insoluble solid was collected to give the desired product, mp 222°–224° C.

EXAMPLE 2

3-(2-Chloroethyl)-5,6-dimethoxyquinazolin-2,4-(1H,3H))dione

This example illustrates the preparation of compounds of formula IV.

A mixture of 3-(2-hydroxyethyl)-5, 6-dimethoxyquinazolin-2, 4-(1H,3H)dione (2.0 g, 0.0075 mole) and thionyl chloride (1.24 g, 0.010 mole) in 20 ml of chloroform was heated at reflux for 4 hours under nitrogen. The solid which formed was washed with chloroform and collected to give the crude product which was recrystallized from methanol to give 1.38 g (64.5% yield) of the desired product, mp 110°–113° C.

EXAMPLE 3

3-{2-[4-(2-Methoxyphenyl)-1-piperazinyl]ethyl}-5,6-dimethoxyquinazolin-2,4-(1H,3H)dione monohydrobromide A mixture of 3-(2-chloroethyl)-5,6-dimethoxyquinazolin-2,4-(1H,3H)dione (5.0 g, 0.018 mole), 1-(2-methoxyphenyl) piperazine (3.4 g, 0.018 mole), sodium iodide (2.64 g, 0.018 mole) and potassium carbonate (1.23 g, 0.009 mole) in 28 ml of dry DMF (dimethylformamide) was heated at 80°–85° C. under nitrogen for 23 hours. Ice-water (75 ml) was then added to the solution and the resultant mixture extracted with chloroform (400 ml). The organics were dried with magnesium sulfate and evaporated in vacuo to give a yellow-brown gummy residue which yielded 4.97 g of an off-white solid upon trituration with ether. Treatment of the crude product with one equivalent of hydrogen bromide in tetrahydrofuran gave the monohydrobromide salt which was purified by washing with hot 2-propanol to give a white solid; yield, 3.72 g. (40%) mp 168°–171°. Treatment of the free base with excess hydrogen bromide gave the dihydrobromide salt, mp 184°–189° C.

EXAMPLE 4

5,6-Dihydroxy-3-{2-[4-(2-methoxyphenyl)-1-piperazinyl]ethyl}-quinazolin-2,4(1H,3H)-dione monohydrobromide monohydrate This example illustrates the hydrolysis of the 5,6-dimethoxy substituted compound to the corresponding 5,6-dihydroxy substituted compound.

A solution of 3-{2-[4-(2-methoxyphenyl)-1-piperazinyl]ethyl}-5,6-dimethoxyquinazolin-2,4-(1H,3H)dione (1.6 g. 2.66M) in hydrobromic acid (48% aqueous, 9.6 ml) and glacial acetic acid (26.2 ml) was heated at reflux for 18 hours. The reaction mixture was cooled and the resulting solid was filtered, washed with ether (30 ml), hexane (30 ml) and dried under high vacuum at 62° C. overnight to give a crude product as a white solid. The crude product was recrystallized from methanol (75 ml). The product was dried under high vacuum at 62° C. for 2 days to afford 5,6-dihydroxy-3-2-[4-(2-methoxyphenyl)-1-piperazinyl]ethyl quinazolin-2,4(1H,3H)-dione (dihydrobromide) as a white solid, (A): 0.72 g (yield 47.1%) mp=283°–286° C. A second crop precipitated out of the filtrate. It was filtered and dried under high vacuum at 62° C. for 6 days to afford additional 5,6-dihydroxy-3-2-[4-(2-methoxy-phenyl)-1-piperazinyl]ethyl quinazolin-2, 4(1H,3H)-dione (monohydrobromide monohydrate) as a white solid: (B) 0.54 g. yield 39.7%, mp=223°–227° C. The total yield of product was 86.8%.

The compounds set forth in Table 1 are prepared by the procedures of Examples 1 through 4 using appropriately substituted starting compounds. The last column of Table 1 indicates the specific example, the procedure of which is utilized to prepare the indicated compound. In Table 1, the final compounds are designated as A through E respectively.

The prior art compound Z set forth at the bottom of Table 1 is that disclosed in the Chugai European Pat. No. 89065-A.

TABLE 1

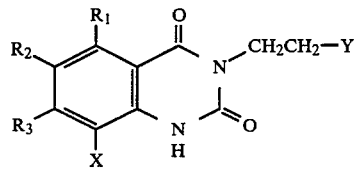

| Compound | R1 | R2 | R3 | X | Y | mp °C. | % Yield | Example No. |
|---|---|---|---|---|---|---|---|---|
| A | OCH3 | OCH3 | H | H | OH | 222–224 | 61 | 1 |

TABLE 1-continued

Structure: substituted benzene with R1, R2, R3, X substituents bearing a -C(O)-N(CH2CH2-Y)-C(O)-NH- fused ring (quinazolinedione-type)

| Compound | R1 | R2 | R3 | X | Y | mp °C. | % Yield | Example No. |
|---|---|---|---|---|---|---|---|---|
|  | OCH₃ | OCH₃ | H | H | Cl | 110–113 | 64.5 | 2 |
|  | OCH₃ | OCH₃ | H | H | -N(piperazine)N-(2-OCH₃-phenyl) | 168–171 (.HBr) 184–189 2(.HBr) | 40 47 | 3 |
| B | OCH₃ | OCH₃ | H | Cl | OH | 197–200 | 71 | 1 |
|  | OCH₃ | OCH₃ | H | Cl | Cl | 171–175 | 77 | 2 |
|  | OCH₃ | OCH₃ | H | Cl | -N(piperazine)N-(2-OCH₃-phenyl) | 167–170 210–210 2(.HCl) | 23 | 3 |
| C | H | OCH₃ | OCH₃ | H | OH | 264–266 | 34 | 1 |
|  | H | OCH₃ | OCH₃ | H | Cl | 283–285 | 84 | 2 |
|  | H | OCH₃ | OCH₃ | H | -N(piperazine)N-(2-OCH₃-phenyl) | 259–261 | 41 | 3 |
| D | OCH₃ | OCH₃ | H | H | -N(piperazine)N-(3-CF₃-phenyl) | 140–142 | 80 | 3 |
|  | OH | OH | H | H | -N(piperazine)N-(2-OCH₃-phenyl) | 223–227 | 40 | 4 |
| E | OCH₃ | OCH₃ | H | H | -N(piperazine)N-(4-OCH₃-phenyl) | 180–182 | 26 | 3 |
| Prior Art Compound Z | H | H | H | H | -N(piperazine)N-(2-OCH₃-phenyl) |  |  |  |

The compounds of the present invention were evaluated for their biological properties. The biological data indicate that certain of the compounds described herein are potent and effective antihypertensive agents. In addition, the data support the concept of unexpected findings regarding side effect liability. For example. Compound A demonstrates significantly less (p 0.05) inhibition of the tilt reflex recovery response than the prior art Chugai compound Z (Compound A: 37%±12 vs. Chugai compound Z: 83%±8). Furthermore, a direct comparison in autonomic tests between Compound A and the Chugai compound Z shows that Compound A possesses almost no antihistaminic or anticholinergic effect, suggesting less side effects such as dryness of mouth, drowsiness or sedation. In contrast, Compound Z inhibits histamine and acetylcholine blood pressure responses in dogs indicating antihistamine and anticholinergic properties. These findings taken together support the contention that Compound A possesses an orally effective antihypertensive profile with the unexpected findings of a more tolerable side effect profile. In addition, the biological data also support the finding of unexpected superior bioavailability, as with compound A when compared with the prior art compound Z, by means of the oral/i.v. ratio (Table 3).

The tilt reflex recovery response is determined as follows:

Adult mongrel dogs of either sex are anesthetized with pentobarbital sodium, secured to a tilt table and surgically prepared for measurement of blood pressure and heart rate. Animals are tilted and the percent recovery of the tilt response in the blood pressure is quantitated.

The percent recovery is calculated by dividing the maximum decrease in mean arterial blood pressure (mm Hg) caused by tilt into the amount of rise in blood pressure at 15 seconds after initiating tilt. The antihypertensive as well as teh alpha$_1$-adrenergic blocking properties of the novel quinazolinedione piperazines were evaluated and set forth in Table 2.

The antihypertensive evaluation followed the following procedure:

Adult male spontaneously hypertensive rats (SHR) were placed in restrainers in a chamber warmed to 32°

C. A standard indirect method employing a pneumatic pulse transducer and inflatable tail cuff was used to measure systolic blood pressure (SBP) in the conscious state. After baseline SBP were recorded, groups of 4 SHR received a single oral dose of drug or vehicle (0.5% methylcellulose) administered with a gavage tube. SBP's were obtained at ½, 1, 2, 3 and 4 hours post treatment. Changes in SBP's were statistically compared to the vehicle effect using Students t test, at p ε0.05.

The $\alpha_1$-adrenergic blockade: inhibition of phenylephrine-induced increases in diastolic blood pressure in the anesthetized dog was determined according to the method set forth in the following literature reference:

Arunlakshana, O, and Schild, H. O. (1959). Some Quantitative Uses of Drug Antagonists. Br. J. Pharmac. Chemother., 14:48–58.

The procedure is as follows:

Dogs are anesthetized and bilaterally vagotomized. A femoral artery and vein are cannulated for detection of diastolic blood pressure and drug administration, respectively. Percent inhibition of alpha adrenergic receptor antagonism is quantitied by determining the dose-response (increase in diastolic pressure) relationship of phenylephrine before and after various doses of the antagonist. Statistical analysis of percent inhibition is calculated by use of the variance component estimation test. In addition, the Dose Ratio (DR$_{20}$) may be calculated for potency comparisons and is defined as the dose of antagonist required to produce an agonist dose ratio of 20.

The biological activity as determined by the above tests, is set forth in Table 2. The tested compounds were the same as those described in detail in Table 1 and referred to as compounds A through E, respectively. The prior art compound set forth at the bottom of Table 2 is that disclosed in the Chugai European Pat. No. 89065-A.

The bioavailability comparison was determined in conscious direct cannulated spontaneously hypertensive rats. Briefly, the SHRs were anesthetized with ether and a carotid arterial catheter was inserted for measurement of arterial blood pressure while a jugular catheter was inserted for i.v. drug administration. For oral dosing, a catheter was also passed via the esophagus into the stomach. All catheters were exteriorized at the nape of the neck and animals were placed in restrainers and allowed to recover from surgery. Blood pressure was continuously recorded. Drugs were dissolved in 5% dextrose in water and administered as a bolus at time zero. Bioavailability results are presented in Table 3.

TABLE 2

| | Antihypertensive and $\alpha_1$-Adrenergic Blocking Properties Of Quinazolinedione Piperazines | | | |
|---|---|---|---|---|
| | Antihypertensive Activity (SHR) | | | $\alpha_1$ Block Dog |
| Compound | Dose (mg/kg PO) | Peak Change in Systolic Blood Pressure | Dose (mg/kg, IV) | Percent Inhibition of Phenylephrin-Induced Pressor Responses |
| A (HBr) | 0.1 | −58 mm Hg | 0.0203 (DR$_{20}$) | 100 |
| | 0.5 | −85 mm Hg | | |
| B | 10 | −72 mm Hg | 0.03 | 60 |
| | | | 0.2 | 93 |
| C | 0.5 | −69 mm Hg | 0.1 | 95 |
| D | 0.05 | −58 mm Hg | 0.0303 | 89 |
| | 0.1 | −60 mm Hg | | |
| E | 20 | −50 mm Hg | 1.0 | 80 |
| Prior Art Compound Z | 0.1 | −40 mm Hg | 0.010 | 100 |

TABLE 3

| | Bioavailability Comparison of Quinazoline dione Piperazines in Spontaneously Hypertensive Rats | | |
|---|---|---|---|
| Compound | I.V. E.D.-10% (a) (mg/kg) | P.O. E.D.-10% (b) (mg/kg) | Ratio (P.O./I.V. (c) |
| A | 1.8 | 70 | 38.9 |
| Z (prior art) | 0.5 | 370 | 740 |

(a) I.V. bolus dose that lowers MABP in conscious SHR by 10%.
(b) Oral gavage dose that lowers MABP in conscious cannulated SHR by 10%.
(c) Bioavailability ratio with small numbers (close to unity) indicating good bioavailability.

What is claimed is:

1. A compound of the formula

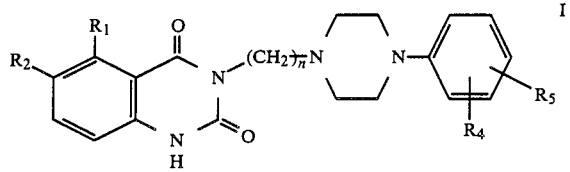

wherein
- $R_1$ is hydroxy or alkoxy having 1–4 carbon atoms:
- $R_2$ is hydroxy or alkoxy having 1–4 carbon atoms: or when $R_1$ and $R_2$ are taken together they are lower alkylenedioxy;
- n is an integer from 2 to 6;
- $R_4$ and $R_5$ are the same or different and are hydrogen, hydroxy, alkyl having 1–6 carbon atoms, alkoxy having 1–4 carbon atoms, halo, or trifluoromethyl, or when $R_4$ and $R_5$ are taken together they are lower alkylenedioxy:

or the pharmaceutically acceptable salts thereof.

2. The compound of claim 1, wherein $R_1$, $R_2$ and $R_4$ are each lower alkoxy having 1–4 carbon atoms and $R_5$ is hydrogen.

3. The compound of claim 1, wherein $R_1$ and $R_2$ are each hydroxyl, and $R_4$ is 2-lower alkoxy having 1–4 carbon atoms.

4. A compound selected from the group consisting of 3-{2-[4-(2-methoxyphenyl)-1-piperazinyl]ethyl}-5,6-dimethoxyquinazolin-2,4 (1H,3H)-dione or the pharmaceutically acceptable salts thereof.

5. A compound selected from the group consisting of 5,6-dihydroxy-3-{2-[4-(2-methoxyphenyl)-1-piperazinyl]ethyl}quinazolin-2,4(1H,3H)-dione or the pharmaceutically acceptable salts thereof.

6. The compound 3-(2-hydroxyethyl)-5,6-dimethoxyquinazolin-2,4-(1H,3H)dione.

7. The compound 3-(2-chloroethyl)-5,6-dimethoxyquinazolin-2,4-(1H,3H)-dione.

8. An antihypertensive composition comprising an inert carrier and as an active ingredient an effective antihypertensive amount of a compound of the formula

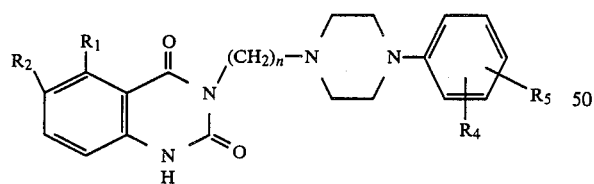

wherein
- $R_1$ is hydroxy or alkoxy having 1–4 carbon atoms:
- $R_2$ is hydroxy or alkoxy having 1–4 carbon atoms: or when $R_1$ or $R_2$ are taken together they are loweralkylenedioxy:
- n is an integer from 2 to 6;
- $R_4$ and $R_5$ are the same or different and are hydrogen, hydroxy, alkyl having 1–4 carbon atoms, alkoxy having 1–4 carbon atoms, halo, or trifluoromethyl, or when $R_4$ and $R_5$ are taken together they are lower alkylenedioxy;

or the pharmaceutically acceptable salts thereof.

9. An antihypertensive composition according to claim 8 wherein said active ingredient is selected from the group consisting of 3-{2-[4-(2-methoxyphenyl)-1-piperazinyl]ethyl}-5,6-dimethoxyquinazolin-2,4(1H,3H)-dione and 5,6-dihydroxy-3-2-[4-(2-methoxyphenyl)-1-piperazinyl]ethyl}quinazolin-2,4(1H,3H)-dione.

10. A pharmaceutical composition useful as an antihypertensive in unit, topical, oral and intravenous dosage forms, comprising from about 0.05 mg/kg to about 100 mg/kg of a compound of claim 1 in admixture with a pharmaceutically acceptable carrier.

11. The composition of claim 10, comprising from about 0.1 mg/kg to about 20 mg/kg of the compound of claim 1, in admixture with the pharmaceutically acceptable carrier.

12. A method of treating hypertension, which comprises administering an effective antihypertensive amount in a pharmaceutically acceptable carrier of a compound of the formula

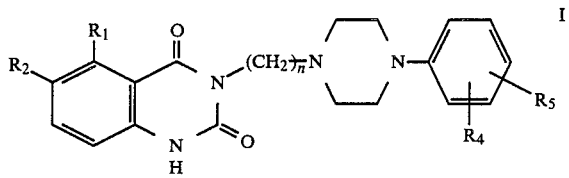

wherein
- $R_1$ is hydroxy or alkoxy having 1–4 carbon atoms:
- $R_2$ is hydroxy or alkoxy having 1–4 carbon atoms: or when $R_1$ or $R_2$ are taken together they are loweralkylenedioxy:
- n is an integer from 2 to 6;
- $R_4$ and $R_5$ are the same or different and are hydrogen, hydroxy, alkyl having 1–4 carbon atoms, alkoxy having 1–4 carbon atoms, halo, or trifluoromethyl, or when $R_4$ and $R_5$ are taken together they are lower alkylenedioxy;

or the pharmaceutically acceptable salts thereof.

* * * * *